United States Patent [19]
Derian et al.

[11] Patent Number: 6,037,407
[45] Date of Patent: Mar. 14, 2000

[54] PROCESS FOR THE PREPARATION OF AQUEOUS EMULSIONS OF SILICONE OILS AND/OR GUMS AND/OR RESINS

[75] Inventors: Paul-Joël Derian, Fontenayaux-Roses; Michel Feder, Lyons; Jean-Pierre Paillet, Feyzin; Michel Peignier, Lentilly; Alain Senechal, Maison-Alfort; Jean Ulrich, Ternay, all of France

[73] Assignee: Rhone Poulenc Chimie, Courbevoie, France

[21] Appl. No.: 09/044,624

[22] Filed: Mar. 19, 1998

Related U.S. Application Data

[62] Division of application No. 08/844,308, Apr. 10, 1997, Pat. No. 5,763,505, which is a continuation of application No. 08/424,323, filed as application No. PCT/FR93/01026, Oct. 19, 1993, abandoned.

[30] Foreign Application Priority Data

Oct. 20, 1992 [FR] France .................... 92/12519

[51] Int. Cl.[7] .................................... B01J 13/00
[52] U.S. Cl. ................ 524/837; 424/401; 516/55
[58] Field of Search ............... 524/837; 516/55; 424/401

[56] References Cited

U.S. PATENT DOCUMENTS

| | | | |
|---|---|---|---|
| 4,788,001 | 11/1988 | Narula | 252/312 |
| 4,814,376 | 3/1989 | Tanaka et al. | 524/588 |
| 5,045,231 | 9/1991 | Braun et al. | 252/315.1 |
| 5,140,061 | 8/1992 | Feder | 524/783 |
| 5,145,901 | 9/1992 | Feder | 524/424 |

FOREIGN PATENT DOCUMENTS

| | | |
|---|---|---|
| 0 200 916 | 11/1986 | European Pat. Off. . |
| 0 270 898 | 6/1988 | European Pat. Off. . |
| 0 404 027 | 12/1990 | European Pat. Off. . |
| 0 463 431 | 1/1992 | European Pat. Off. . |
| 1191289 | 5/1970 | United Kingdom . |
| 1523678 | 9/1978 | United Kingdom . |

OTHER PUBLICATIONS

Dr. Otto–Albrecht Neumüller, Römpps Chemie–Lexikon, Franhck'sche Verlagshadlung Stuggart, HMO–Theorie, p. 1715 (1983).

Wolfgang Gerhartz et al., Ullmann's Encyclopedia of Industrial Chemistry, Emulsions, vol. A9, p. 297, 325 (1987).

Dr. Heinrich Grossmann et al., Tensid–Taschenbuch, Carl Hanser Verlag München Wien, p. 14–15 (1990).

*Primary Examiner*—Margaret G. Moore
*Attorney, Agent, or Firm*—Scully, Scott, Murphy & Presser

[57] ABSTRACT

A cosmetic composition comprising an aqueous emulsion of organopolysiloxanes selected from the group consisting of silicone oils, gums, resins and mixtures therein which is prepared in a single kneading step which is sufficient to produce an emulsion having a particle size of 0.1 to 5 micrometers is provided.

1 Claim, No Drawings

PROCESS FOR THE PREPARATION OF AQUEOUS EMULSIONS OF SILICONE OILS AND/OR GUMS AND/OR RESINS

RELATED APPLICATIONS

This application is a divisional application of U.S. patent application Ser. No. 08/844,308, filed Apr. 10, 1997, now U.S. Pat. No. 5,763,505, which was a continuation of 08/424,323, abandoned, which was filed Jul. 14, 1995. This application claims benefits to PCT/FR93/01026, filed Oct. 19, 1993.

The subject of the present invention is a process for the preparation of the emulsions of silicone oils and/or gums and/or resins which are preferably viscous.

DISCUSSION OF THE PRIOR ART

It has been proposed (British Patent 1,191,289) to emulsify viscous silicone oils (5,000–1,000,000 mPa·s) by kneading a mixture of oil, 1–10% of surface-active agent and 10–20% of water using a roll-mill mixer equipped with at least two rollers; such a process has the disadvantage of using equipment of low productivity which additionally presents safety problems, which makes it difficult to be operated industrially.

European Application EP-A-463,431 describes the preparation of aqueous emulsions of silicone oils, especially of high viscosity, by separate introduction, in two stages, of two types of surface-active agents of different HLB values into a conventional kneading device.

SUMMARY OF THE INVENTION

The Applicant company has found a process for the preparation of aqueous emulsions of viscous phases based on silicone oils and/or gums and/or resins, which are preferably viscous, which uses a conventional kneading device and which does not require the mandatory use of two types of surface-active agents.

Such a process makes it possible to prepare emulsions of silicone oils and/or gums and/or resins with a perfectly controlled and relatively homogeneous particle size.

DETAILED DESCRIPTION OF THE INVENTION

The process for the preparation of emulsions of silicone oils and/or gums and/or resins which forms the subject of the invention is characterized in that a mixture comprising
  100 parts by weight of a silicone phase (A) with a dynamic viscosity at 25° C. at least equal to 3 Pa·s, preferably at least equal to 30 Pa·s, or with a consistency at 25° C. of less than 2,000, the silicone phase comprising at least one polyorganosiloxane oil and/or gum and/or resin;
  2 to 20 parts by weight, preferably from 3 to 15 parts by weight, of water;
  3 to 20 parts by weight, preferably from 5 to 15 parts by weight, of at least one surface-active agent (B) or a combination of 0.5 to 10 parts by weight, preferably from 1 to 10 parts by weight, of at least one surface-active agent (B) and of $2.5 \times 10-10^{-4}$ to 20 parts by-weight, preferably from 0.001 to 15 parts by weight, of at least one water-soluble thickening polymer (C) with a molecular mass greater than 10,000 g/mol and preferably greater than 100,000 g/mol, is kneaded, the said surface-active agent or mixture of surface-active agents having an HLB value of at least 10 and the relative amounts of water, constituent(s) (B) and optionally (C) being such that the viscosity or the consistency of the water+surface-active agent(s)+ optional water-soluble thickening polymer(s) mixture is in the region of or greater than one-tenth of the viscosity or consistency of the silicone phase (A) and preferably in the region of or greater than the viscosity or consistency of the silicone phase (A); the said kneading being carried out for a period of time and under shearing conditions which are sufficient to produce an emulsion of "oil-in-water" type with a particle size of the order of 0.1 to 5 micrometers and preferably of the order of 0.2 to 3 micrometers;

in that, when a mixture of surface-active agents comprising at least one non-ionic surface-active agent is present, the said mixing is carried out in a single stage;

and then in that the medium is optionally diluted with water according to the desired solids content.

For good implementation of the invention, the dynamic viscosity is preferably measured at 25° C. using a Brookfield viscometer according to AFNOR standard NFT 76 102 of February 1972; the determination of the consistency can be carried out by measuring the penetrability using a penetrometer, for example according to one of the standards AFNOR NFT 60 119, NFT 60 123, NFT 66 004, ASTM D 217, D 937, D 1321 or D 5.

Mention may be made, as examples of silicone phases (A) which can be used, of those comprising:

a polyorganosiloxane oil and/or gum and/or resin with a viscosity at least equal to 3 Pa·s, preferably of the order of 30 to 2,500 Pa·s, or with a consistency of the order of 200 to 2,000.

a mixture of polyorganosiloxane oil(s) and/or gum(s) and/or resin(s), which mixture has a viscosity at least equal to 3 Pa·s, preferably of the order of 30 to 2,500 Pa·s, or a consistency of the order of 200 to 2,000.

a mixture of polyorganosiloxane oil(s) and/or gum(s) and/or resin(s) and of at least one solvent of the said oil and/or gum and/or resin and/or of at least one silane and/or of at least one siliceous or non-siliceous filler, which mixture has a viscosity at least equal to 3 Pa·s, preferably of the order of 30 to 2,500 Pa·s, or a consistency of the order of 200 to 2,000.

Mention may be made, among the polyorganosiloxane oils and gums which can be used, of those comprising the units of formula

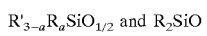

in which formulae
  a is an integer from 0 to 3
  the R radicals are identical or different and represent
    a saturated or unsaturated aliphatic hydrocarbon group containing from 1 to 10 carbon atoms;
    an aromatic hydrocarbon group containing from 6 to 13 carbon atoms;
    a polar organic group bonded to the silicon by an Si—C or Si—O—C bond;
    a hydrogen atom;
  the R' radicals are identical or different and represent
    an OH group
    an alkoxy or alkenyloxy group containing from 1 to 10 carbon atoms;
    an aryloxy group containing from 6 to 13 carbon atoms;

an acyloxy group containing from 1 to 13 carbon atoms a ketiminoxy group containing from 1 to 8 carbon atoms an amino- or amidofunctional group containing from 1 to 6 carbon atoms, bonded to the silicon by an Si—N bond preferably at least 80% of the R radicals of the said oils representing a methyl group.

Mention may be made, among the polyorganosiloxane resins which can be used, of those comprising units of formulae $RSiO_{3/2}$ (T unit) and/or $SiO_2$ (Q unit)

in combination with units of formula $R'_{3-a}R_aSiO_{1/2}$ (M unit) and/or $R_2SiO$ (D unit)

in which formulae a, R and R' have the definition given above.

The latter are generally of the MQ, MDQ, TDM, TD or MT type.

Mention may be made, as examples of aliphatic or aromatic hydrocarbon radicals R, of the following groups:

alkyls, such as for example methyl, ethyl, octyl or trifluoropropyl alkoxyalkylene, such as for example —$CH_2$—$CH_2$—O—$CH_3$ or —$CH_2$—$CH_2$—O—$CH_3$, alkenyls, such as for example vinyl, allyl, hexenyl, decenyl or decadienyl alkenyloxyalkylene, such as —$(CH_2)_3$—O—$CH_2$—$CH=CH_2$ or —$(CH_2)_3$—$OCH_2$—$CH_2$—O—$CH=CH_2$, aryls, such as for example phenyl.

Mention may be made, as examples of polar organic groups R, of:

hydroxyfunctional groups such as for example —$(CH_2)_3$—OH, —$(CH_2)_4N(CH_2CH_2OH)_2$ or —$(CH_2)_3$—N$(CH_2CH_2OH)$—$CH_2$—$CH_2$—$N(CH_2CH_2OH)_2$, aminofunctional groups such as for example —$(CH_2)_3$—$NH_2$ or —$(CH_2)_3$—NH—$(CH_2)_2NH_2$, amidofunctional groups such as for example —$(CH_2)_3$—N—$(COCH_3)$—$(CH_2)_2NH(COCH_3)$, carboxyfunctional groups such as for example —$CH_2$—$CH_2$—S—$CH_2$—COOH.

Mention may be made, as examples of R' radicals, of the following groups:

alkoxy, such as methoxy, ethoxy, octyloxy, and the like alkenyloxy, such as vinyloxy, hexenyloxy, isopropenyloxy, and the like aryloxy, such as phenyloxy, and the like acyloxy, such as acetoxy, and the like ketiminoxy, such as $ON=C(CH_3)C_2H_5$, and the like aminofunctional, such as ethylamino, phenylamino, and the like amidofunctional, such as methylacetamido, and the like.

Mention may be made, as concrete examples of "D units", of:

$(CH_3)_2SiO$, $CH_3(CH=CH_2)SiO$, $CH_3(C_6H_5)SiO$, $(C_6H_5)_2SiO$, $CH_3HSiO$, $CH_3(CH_2—CH_2—CH_2OH)SiO$, and the like.

Mention may be made, as concrete examples of "M units", of:

$(CH_3)_3SiO_{1/2}$, $(CH_3)_2(OH)SiO_{1/2}$, $(CH_3)_2(CH=CH_2)SiO_{1/2}$, $(CH_3)_2HSiO_{1/2}$, $(OCH_3)_3SiO_{1/2}$, $[O—C(CH_3)=CH_2]_3SiO_{1/2}$, $[ON=C(CH_3)]_3SiO_{1/2}$, $(NH—CH_3)_3SiO_{1/2}$, $(NH—CO—CH_3)_3SiO_{1/2}$, and the like.

Mention may be made, as concrete examples of "T units", of:

$CH_3SiO_{3/2}$, $(CH=CH_2)SiO_{3/2}$, $HSiO_{3/2}$, and the like.

When the said oils, gums or resins contain reactive and/or polar R radicals (such as H, OH, vinyl, allyl, hexenyl, aminoalkyl, and the like), the latter generally do not represent more than 2% of the weight of the oil or gum and not more than 10% of the weight of the resin.

Viscous polydimethylsiloxane and $\alpha,\omega$-bis(hydroxy) polydimethylsiloxane oils, as well as polydimethylsiloxane, polyphenylmethylsiloxane and $\alpha,\omega$-bis(hydroxy) polydimethylsiloxane gums, are well known commercial products.

Viscous DT polymethylsiloxane resins containing from 1 to 2% by weight of silanol functional groups are also commercial products.

Mention may be made, among the solvents of silicone oils, gums or resins which are optionally present in the silicone phase, of volatile cyclic organopolysiloxanes (octamethylcyclotetrasiloxane, decamethylcyclopentasilbxane, and the like), short polydimethylsiloxane oils (viscosity less than 100 mPa·s), hexamethyldisiloxane, ketones (methyl ethyl ketone, and the like), ethers (diethyl ether, and the like), esters (isopropylmyristate, ethyl acetate, and the like), some chlorinated or chlorofluorinated solvents (methylene chloride, chloroform, and the like) or highly branched paraffins (white oils based on isoalkanes and cycloalkanes, and the like).

According to the present invention, various inorganic fillers and/or silanes can additionally be present in the silicone phase to be emulsified.

These silanes can especially be by-products from the synthesis of the said polyorganosiloxane oils, gums or resins used or crosslinking agents of the said oils, gums or resins.

They can be represented by the formula $(R_b)Si(OR')_{4-b}$, in which formula b is an integer from 0 to 4, R and R' having the definition given above. They are especially described in U.S. Pat. No. 3,294,725, U.S. Pat. No. 4,584,341, U.S. Pat. No. 4,618,642, U.S. Pat. No. 4,608,412, U.S. Pat. No. 4,525,565, EP-A-340,120, EP-A-364,375, FR-A-1,248,826, FR-A-1,423,477 and EP-A-387,157.

Mention may be made, as examples, of the following silanes:

$Si(OC_2H_5)_4$, $CH_3Si(OCH_3)_3$, $CH_3Si(OC_2H_5)_3$, $(C_2H_5O)_3Si(OCH_3)$, $CH_2=CHSi(OCH_3)_3$, $CH_3(CH_2=CH)Si(OCH_3)_2$, $CH_2=CHSi(OC_2H_5)_3$, $CH_2=CHSi[ON=C(CH_3)C_2H_5]_3$, $CH_3Si[ON=C(CH_3)_2]_3$, $CH_3Si[O—C(CH_3)=CH_2]_3$, methyltris(N-methylacetamido)silane or methyltris(cyclohexylamino)silane.

They are generally present in amounts of the order of 0 to 10 parts by weight, preferably of the order of 0 to 5 parts by weight, per 100 parts by weight of polyorganosiloxane oil(s) and/or gum(s) and/or resin, when they are reaction by-products. When their function as crosslinking agent of hydroxylated oils, gums or resins is sought, they are generally present in amounts of the order of 0.5 to 30 parts by weight, preferably of the order of 2 to 8 parts by weight, per 100 parts by weight of oil(s) and/or gum(s) and/or resin(s).

The said silanes can also be an additive which makes it possible to modulate the physicochemical properties, especially the adhesion properties, of the silicone compositions of various applications obtained from the aqueous emulsions prepared according to the process of the invention. Examples of such silanes are especially described in EP-A-340,120. Mention may be made, from this category of silanes, of for example aminopropyltriethoxysilane, aminopropylmethyl-diethoxysilane or glycidoxypropyltrimethoxysilane. They are used in amounts which can range up to 200%, generally of the order of 2 to 100%, of the weight of oil(s) and/or gum(s) and/or resin(s).

Reinforcing or semi-reinforcing siliceous or non-siliceous fillers may be present according to the invention; mention may be made, as example, of colloidal silicas, precipitated and fumed silica powders, diatomaceous earths, ground quartz, natural calcium carbonate, alumina hydrate, magnesium hydroxide, carbon black, titanium dioxide, aluminium oxide, vermiculite, zinc oxide, mica, talc, iron oxide, barium sulphate or slaked lime; the particle size of these fillers is generally of the order of 0.001 to 300 $\mu$m; they are generally present in amounts which can range up to 300%, preferably of the order of 3 to 100%, of the weight of oil(s) and/or gum(s) and/or resin(s).

The surface-active agents (B) used can be non-ionic, with an HLB value greater than 10 and preferably of the order of 10 to 20, anionic, cationic, zwitterionic or amphoteric, with an HLB value greater than 10.

The non-ionic surface-active agents can be chosen from for example alkoxylated fatty acids, polyalkoxylated alkylphenols, polyalkoxylated fatty alcohols, polyalkoxylated or polyglycerolated fatty amides, polyglycerolated alcohols and $\alpha$-diols or ethylene oxide-propylene oxide block copolymers, as well as alkylglucosides, alkylpolyglucosides, sugar ethers, sugar esters, sugar glycerides or sorbitan esters, and the ethoxylated compounds of these sugar derivatives, having an HLB value of at least 10.

The anionic surface-active agents can be chosen from for example alkylbenzenesulphonates, alkyl sulphates, alkyl ether sulphates, alkylaryl ether sulphates, dialkyl sulphosuccinates, alkyl phosphates or ether phosphates of alkali metals having an HLB value of at least 10.

Mention may be made, among cationic surface-active agents, of for example aliphatic or aromatic fatty amines, aliphatic fatty amides or quaternary ammonium derivatives having an HLB value of at least 10.

Mention may be made, among zwitterionic or amphoteric surface-active agents, of for example betaines and their derivatives, sultaines and their derivatives, lecithins, imidazoline derivatives, glycinates and their derivatives, amidopropionates or fatty amine oxides having an HLB value of at least 10.

The (mixture of) surface-active agent(s) is chosen as a function of the nature of the polyorganosiloxane oil and/or gum and/or resin; an HLB value of the order of 11 to 15 is generally chosen in order to emulsify a silicone oil or gum (A) comprising an $\alpha,\omega$-bis(trimethyl)polydimethylsiloxane or an $\alpha,\omega$-bis(hydroxy)polydimethylsiloxane; however, ionic surface-active agents with an HLB value greater than 20 are also suitable.

The thickening polymers (C) are soluble to at least 50% in water; mention may be made, as examples of thickening polymers, of
- those obtained by chemical synthesis, such as for example poly(vinyl alcohol)s, poly(ethylene glycol)s, polyvinylpyrrolidones or alkali metal polyacrylates,
- those extracted from plants and optionally modified, such as for example carrageenans, alginates, carboxymethyl celluloses, methyl celluloses, hydroxypropyl celluloses or hydroxyethyl celluloses,
- those obtained by biosynthesis, such as for example xanthan gum.

The relative amounts of water, surface-active agent(s) and optional thickening polymer(s) are functions of the viscosity of the silicone phase comprising at least one polyorganosiloxane oil and/or gum and/or resin, as well as of the nature of the (mixture of) surface-active agent(s) and of the nature of the (mixture of) optional thickening polymer(s). In the absence of thickening polymer, the water/water+surface-active agent(s) ratio by weight is, for example, of the order of 20/100 to 70/100, preferentially of the order 25/100 to 60/100, in order to stabilize an emulsion of a silicone phase comprising an $\alpha,\omega$-bis(trimethyl)- or -(hydroxy) polydimethyl-siloxane oil with a viscosity of the order of 30 Pa·s to 500 Pa·s, using a nonylphenol having 9 or 10 ethoxy units as sole surface-active agent. The use of an aqueous phase comprising water and sodium dodecyl sulphate as sole surface-active agent, according to a water/water $\downarrow$ surface-active agent ratio by weight of 5/7 and containing from 0.5 to 2% of its weight of hydroxyethyl cellulose as thickening polymer, makes possible the stabilization of $\alpha,\omega$-bis (trimethyl)polydimethylsiloxane oils with a viscosity of the order of 5 Pa·s to 30 Pa·s.

The operation of emulsifying the silicone phase can be carried out by
- introduction of at least one oil and/or gum and/or resin+optional solvent(s)+optional silane(s) into a water+surface-active agent(s)+optional water-soluble polymer(s) mixture, the optional filler(s) being present in the aqueous mixture and/or introduced into the said mixture, and then kneading at a temperature of the order of 10 to 50 ° C.;
- or preferably introduction of the water into an oil(s) and/or gum(s) and/or resin(s), entirely or partially present [for example, 50–90% of the total amount of oil(s) and/or gum(s) and/or resin(s)],+optional solvent(s)+optional silane(s)+optional filler(s)+surface-active agent(s)+optional water-soluable polymer(s) mixture and then kneading at a temperature of the order of 10 to 50° C., the optionally remaining amount of oil(s) and/or gum(s) and/or resin(s) being introduced into the medium after the formation of the "oil-in-water" emulsion while continuing to knead.

Any conventional kneading device can be used, especially slow-stirring devices. Thus, the kneading operation can be carried out in a mixer equipped with a stirrer, a stirrer in which the moving part does not rotate at more than 2,500 revolutions/min (preferably at not more than 1500 revolutions/min and very particularly at not more than 500 revolutions/min) with a tangential speed at the end of the moving part not exceeding 20 m/s (preferably not exceeding 5 m/s and very particularly not exceeding 2.5 m/s); advantageously, the tangential speed at the end of the moving part/distance between the end of the moving part and the wall of the mixer ratio is less than 50,000 s$^{-1}$, preferably less than 10,000 s$^{-1}$ and very particularly less than 2,500 s$^{-1}$.

Mention may be made, as examples, of single- or multiple-screw extruders, planetary mixers, hook mixers, slow dispersers, static mixers or paddle, propeller, arm or anchor mixers.

The viscous silicone oil and/or gum and/or resin emulsions obtained according to the process of the invention are particularly stable on storage; they can be very fine and monodisperse; their solids content can range from 25 (or less, depending on the targeted application of the said emulsions) to 98%, it being possible for the solids content to be adjusted by dilution.

They can be used for the preparation of silicone-based compositions which adhere to surfaces made of various materials such as glass, concrete or wood, for the preparation of cosmetic products (shampoos, creams, conditioning agents, liquid soaps or other body hygiene products), of industrial or domestic cleaning products, of domestic descaling products, of surface polishing products (for example for the car) or of polishes (for example for shoes) or for the softening treatment of textiles.

The examples are given by way of indication and may not be regarded as a limit to the scope and spirit of the invention.

EXAMPLE 1

The following are introduced into a 5 liter arm mixer of Kustner® type (marketed by Kustner):

1,500 g of α,ω-bis(hydroxy)polydimethyl-siloxane oil with a viscosity equal to 175 Pa·s (48 V 175000 oil)

then 75 g of Cemulsol NP 9® (nonylphenol containing 9 ethoxy units marketed by Rhône-Poulenc) having an HLB value of 12.8.

The medium is stirred for approximately 15 minutes at 90 revolutions/minute.

100 g of water are then slowly run in over approximately 10 minutes with the same stirring and the medium is then kneaded with the same stirring for approximately 150 minutes; the water/water+surface-active agent ratio by weight is 0.57 (the dynamic viscosity of this 75/100 surface-active agent/water mixture is 380 Pa·s at a shear gradient of $1\ s^{-1}$). The development in the mean particle size of-the emulsion formed, as a function of the kneading time, is monitored using a Coulter N4S® particle sizer (marketed by Coultronics).

The final emulsion is then diluted with 584 g of water in order to obtain a solids content of 70%.

EXAMPLE 2

The operation described in Example 1 is repeated using 50 g of water, introduced over approximately 5 minutes, in place of 100 g, which corresponds to a water/water+surface-active agent ratio of 0.4.

It is observed, from the following Table 1, that the emulsion more rapidly becomes fine.

TABLE 1

| duration of kneading after introduction of water | mean particle size (in nanometers) | |
| --- | --- | --- |
| (in minutes) | Example 1 | Example 2 |
| 30 | 1700 | 473 |
| 60 | 1490 | 413 |
| 90 | 567 | 373 |
| 120 | 437 | — |
| 150 | 375 | 340 |

EXAMPLE 3

The following are introduced into a 250 $cm^3$ reactor equipped with an anchor stirrer system:

2.5 g of Siponic L4® marketed by Rhône-Poulenc 2.5 g of water.

The mixture is stirred at 150 revolutions/min for 5 minutes.

A thick paste is formed to which is added, over approximately 20 minutes, with stirring at approximately 350 revolutions/min, 87 g of 70641 V 500000 polydiphenyldimethylsiloxane oil (viscosity of 500,000 mPa·s). At the end of the introduction of the oil, the mixture is kneaded with the same stirring for approximately 15 minutes. An emulsion having a solids content of 70% and a particle size of 2.76 μm is obtained.

EXAMPLE 4

The operation described in Example 1 is repeated from:

a 1500 g of α,ω-bis(hydroxy)polydimethyl-siloxane oil with a viscosity of 70 Pa·s 75 g of Cemulsol NP 9

75 g of water, introduced over approximately 5 min, which corresponds to a water/water+surface-active agent ratio of 0.5.

The mean particle sizes of the emulsion obtained after 30, 60 and 90 minutes of kneading at 90 revolutions/minute are respectively 600, 487 and 495 nanometers.

The final emulsion is diluted with 568 g of water in order to obtain a solids content of 71%.

EXAMPLE 5

The operation described in Example 1 is repeated from 1500 g of 48 V 175000 oil 150 g of Cemulsol NP 9

150 g of water, introduced over approximately 10 min.

After kneading for 90 minutes at 90 revolutions/minute, a stable 380 nm emulsion is obtained.

The latter is diluted to a solids content of 75% by the addition of 555 g of water and rekneaded for 20 minutes.

EXAMPLE 6

The following are introduced into the mixer of Example 1

1500 g of 48 V 175000 oil 37.5 g of Cemulsol NP 5® (nonylphenol containing 5 ethoxy units marketed by Rhône-Poulenc)

112.5 g of Cemulsol NP 12® (nonylphenol containing 12 ethoxy units marketed by Rhône-Poulenc). The mixture of surface-active agents has an HLB value of 13. After kneading for 20 minutes at 90 revolutions/minute, 100 g of water are added over approximately 6 min; kneading is carried out under the same conditions for 1 hour; an additional 30 g of water are added over approximately 2 min and stirring is carried out under the same conditions for 1 hour. The mean particle size of the emulsion obtained is 580 nm. The emulsion is brought to a solids content of 75% by dilution with 470 g of water.

EXAMPLE 7

The following are introduced into the mixer of Example 1

1500 g of 48 V 175000 oil a mixture, heated beforehand to 50° C., of 45 g of Genapol X 050® (ethoxylated fatty alcohol marketed by Hoechst)

45 g of Genapol UD 110® (ethoxylated fatty alcohol marketed by Hoechst)

The surface-active mixture agent mixture has an HLB value of 12.5.

After kneading for 20 minutes at 90 revolutions/minute, 105 g of water are introduced over approximately 6 min. While kneading at 90 revolutions/minute, an emulsion is obtained which contains two populations; the development in the mean particle size of the emulsion as a function of the kneading time appears in Table 2. The solids content of the final emulsion is adjusted to 76% by addition of 440 g of water and rekneading at 90 revolutions/minute for 20 minutes.

TABLE 2

| duration of kneading (minutes) | 30 | 60 | 90 | 120 |
|---|---|---|---|---|
| 1st population, mean Ø (nm.) | 1530 | 1500 | 949 | 785 |
| proportion (%) | 78 | 83 | 89 | 95 |
| 2nd population, mean Ø (nm.) | 573 | 433 | 303 | 298 |
| proportion (%) | 22 | 17 | 11 | 5 |

EXAMPLE 8

Preparation of a Viscous Methoxyfunctional Oil

The following are introduced into the mixer of Example 1

1500 g of 48 V 175000 oil 15 g of vinyltrimethoxysilane

After stirring for 10 minutes at 90 revolutions/minute, 7.95 g of a 3.75% methanolic lithium hydroxide (LiOH.H$_2$O) solution are added; stirring is carried out for 25 minutes under the same conditions before neutralizing the mixture by addition of 6 g of the reaction product of phosphoric acid with octamethyl-cyclotetrasiloxane, which assays at 8.5% of H$_3$PO$_4$.

Emulsification of the Methoxyfunctional Oil

A mixture of 75 g of Cemulsol NP 5 and 75 g of Cemulsol NP 12 is added to the oil obtained.

The mixture of surface-active agents has an HLB value of 12.

The medium is kneaded at 90 revolutions/minute for 10 minutes; 130 g of water are slowly added over approximately 8 min and kneading is then carried out for 90 minutes at 90 revolutions/minute.

An emulsion with a mean particle size of 535 nm is obtained, which emulsion is diluted with 420 g of water.

EXAMPLE 9

Preparation of a Viscous Methoxyfunctional Oil

The operation described in Example 8 is repeated using 45 g of vinyltrimethoxysilane in place of 15 g.

Emulsification of the Methoxyfunctional Oil 150 g of Cemulsol NP 7® (nonylphenol containing 7 ethoxy units marketed by Rhône-Poulenc), with an HLB value=11.7, are added to the oil obtained. Kneading is carried out for 5 minutes at 90 revolutions/minute, 160 g of water are then added over approximately 10 min and kneading is carried out for 90 minutes at 90 revolutions/minute.

The emulsion obtained has a mean particle size of 1670 nm; it is then diluted by addition of 390 g of water.

EXAMPLE 10

The following are introduced into the mixer of Example 1

1525 g of 48 V 175000 oil 15 g of (N-methyl-3-aminopropyl)trimethoxy-silane.

The mixture is kneaded for 20 minutes at 90 revolutions/minute and then placed under slight vacuum for 5 minutes.

A premix containing 70 g of Cemulsol NP 5 and 70 g of Cemulsol NP 9 is added.

The mixture of surface-active agents has an HLB value of 11.4.

Kneading is carried out for 10 minutes at 90 revolutions/minute and then 120 g of water are introduced over approximately 7 min with stirring; the mixture is kneaded for 45 minutes at 90 revolutions/minute.

The emulsion obtained has a mean particle size of 2400 nm.

30 g of water are added over approximately 3 min and kneading is continued under the same conditions for 90 minutes; the particle size is then 1790 nm. The emulsion is diluted with 400 g of water in order to, have a solids content of 74%.

EXAMPLE 11

Preparation of a Methoxyfunctional oil

The following are introduced into the mixer of Example 1:

1500 g of 48 V 175000 Oil 45 g of vinyltrimethoxysilane.

After stirring for 5 minutes at 90 revolutions/min, 12 g of a 3.75% methanolic lithium hydroxide solution are added; stirring is carried out for 20 minutes at 90 revolutions/min and then the mixture is neutralized with 9 g of the reaction product of phosphoric acid with octamethyltetracyclosiloxane, which assays at 8.5% of H3PO4.

After stirring for 15 minutes under the same conditions, deaeration is carried out under vacuum for 15 minutes.

Emulsification of the Methoxyfunctional Oil

A mixture of 75 g of Cemulsol NP 5 and 75 g of Cemulsol NP 12 is added to the oil thus obtained.

Stirring is carried out for 5 minutes at 90 revolutions/min and then 130 g of water are introduced over approximately 8 min.

After kneading for 90 minutes at 90 revolutions/minute, an emulsion with a mean particle size of 630 nm is obtained.

It is then diluted by addition of 420 g of water.

EXAMPLE 12

The following are introduced into a 250 cm$^3$ reactor equipped with a scraping paddle stirrer system:

5.6 g of Soprophor NP 10® (nonylphenol ethoxylated with 10 ethylene oxide units marketed by Rhône-Poulenc) with an HLB value of 13.3

3 g of Aerosil 200® hydrophilic silica (marketed by Degussa), the particle size of which is 0.012 micrometer 8.4 g of water.

The mixture is stirred at 150 revolutions/min for 5 minutes.

A thick paste is formed to which are added, over approximately 20 minutes, with stirring at approximately 350 revolutions/min, 83 g of α,ω-bis(hydroxy)polydimethylsiloxane oil with a viscosity equal to 70 Pa·s (48 V 70000 oil). At the end of the introduction of the oil, the mixture is kneaded with the same stirring for approximately 45 minutes. An emulsion having a solids content of 91.6% and a particle size of 1.14 micrometers is obtained.

EXAMPLE 13

The operation described in Example 12 is repeated using on the one hand,
- 5 g of Soprophor NP 10
- 6 g of Aerosil 200® silica (marketed by Degussa)
- 9 g of water and, on the other hand, 80 g of 48 V 70000 oil.

The emulsion obtained has a solids content of 91% and a particle size of 1.06 micrometers.

EXAMPLE 14

The operation described in Example 12 is repeated using on the one hand,
- 4.9 g of Soprophor NP 10
- 6 g of Tixosil 3750 hydrophilic silica (marketed by Rhône-Poulenc) with a particle size of 1.6 micrometers
- 9 g of water and, on the other hand, 81 g of 48 V 70000 oil.

The emulsion obtained has a solids content of 91.9% and a particle size of 0.99 micrometer.

EXAMPLE 15

The following are introduced into a 250 cm$^3$ reactor equipped with a scraping paddle stirrer system:
- 5 g of Soprophor NP 10®
- 7 g of water.

The mixture is stirred at 150 revolutions/min for 5 minutes.

A thick paste is formed to which are added, over approximately 20 minutes, with stirring at approximately 350 revolutions/min, 85 g of 48 V 70000 oil and 3 g of Tixosil 375 hydrophilic silica. At the end of the introduction of the oil and silica, the mixture is kneaded with the same stirring for approximately 45 minutes. An emulsion having a solids content of 93% and a particle size of 1.16 micrometers is obtained.

EXAMPLE 16

The following are introduced into a 250 cm$^3$ reactor equipped with a scraping paddle stirrer system:
- 6.3 g of Soprophor NP 10®
- 7.7 g of water (the dynamic viscosity of this surface-active agent/water mixture, at a shear gradient of 1 s$^{-1}$, is of the order of 300 Pa·s).

The mixture is stirred at 150 revolutions/min for 5 minutes.

A thick paste is formed, to which are added, over approximately 20 minutes, with stirring at approximately 350 revolutions/min, 86 g of 48 V 70000 oil. At the end of the introduction of the oil, the mixture is kneaded with the same stirring for approximately 75 minutes. An emulsion having a solids content of 92.3% is obtained.

The development in the mean particle size as a function of the kneading time is given in Table 3.

EXAMPLE 17

The operation described in Example 16 is repeated from on the one hand,
- 6.3 g of Cemulsol NP 10® with an HLB value of 13.3
- 7.7 g of water and, on the other hand, 86 g of α,ω-bis(trimethyl) polydimethylsiloxane oil having a viscosity of 100 Pa·s (47 V 100000 oil).

The emulsion obtained has a solids content of 92.3%. The development in the mean particle size as a function of the kneading time is given in Table 3.

EXAMPLE 18

The operation described in Example 16 is repeated from on the one hand,
- 5 g of Cemulsol NP 10® with an HLB value of 13.3
- 5 g of water (the dynamic viscosity of this surface-active agent/water mixture, at a shear gradient of 1 s$^{-1}$, is 253 Pa·s)

and, on the other hand, 90 g of α,ω-bis(trimethyl) polydimethylsiloxane oil having a viscosity of 500 Pa·s (47 V 500000 oil).

The emulsion obtained has a solids content of 95%. The development in the mean particle size as a function of the kneading time is given in Table 3.

EXAMPLE 19

The operation described in Example 16 is repeated from on the one hand
- 6.3 g of Cemulsol NP 10® with an HLB value of 13.3
- 7.7 g of water and, on the other hand, 86 g of a 40% by weight solution in decamethylcyclopentasiloxane (D5) of Gomme FB® (α,ω-bis(trimethyl) polydimethylsiloxane gum having a consistency of the order of 700 to 1000, marketed by Rhône-Poulenc); this gum solution has a viscosity of 500 Pa·s.

The emulsion obtained has a solids content of 92.3%. The development in the mean particle size as a function of the kneading time is given in Table 3.

TABLE 3

| duration of kneading (in min) | mean particle size (in μm) Example | | | |
|---|---|---|---|---|
| after introduction of the oil | 16 | 17 | 18 | 19 |
| 15 | 1.21 | 1.21 | 2.77 | 1.38 |
| 30 | | 1.16 | | |
| 45 | 1.10 | 1.07 | 1.65 | 1.26 |
| 75 | 1.09 | 1.05 | 1.53 | 1.11 |

EXAMPLE 20

The following are introduced into a 250 cm$^3$ reactor equipped with a scraping paddle stirrer system:
- 6.3 g of Cemulsol NP 10®
- 7.7 g of water.

The mixture is stirred at 150 revolutions/min for 5 minutes.

A thick paste is formed to which are added, using a push pump situated at the bottom of a reactor, 86 g of Gomme FB, over approximately 20 minutes, with stirring at approximately 350 revolutions/min. At the end of the introduction of the oil, the mixture is introduced into the trough of a Brabender® farinograph (marketed by Brabender) equipped with two scraping kneading helices and kneaded for a number of hours. An emulsion having a solids content of 92.3% is obtained. The development in the mean particle size as a function of the kneading time is given in Table 4.

TABLE 4

| duration of kneading in the Brabender mixer (in hours) | 1 | 3 | 6 | 26 |
|---|---|---|---|---|
| mean particle size (in micrometers) | 6.42 | 3.97 | 2.93 | 1.99 |

EXAMPLE 21 (comparative)

The operation described in Example 17 is repeated from
on the one hand,
- 3 g of Cemulsol NP 10
- 11 g of water (the viscosity of this aqueous medium is approximately 10 mPa·s)

and, on the other hand, 86 g of 47 V 100000 oil.

The emulsion obtained has a mean particle size of greater than 30 micrometers, with millimeter droplets.

EXAMPLE 22 (comparative)

The operation described in Example 16 is repeated from
x
on the one hand
- 3 g of Cemulsol NP 10
- 11 g of water and, on the other hand, 86 g of α,ω-bis(trimethyl) polydimethylsiloxane oil having a viscosity of 30 Pa·s (47 V 30000 oil).

The emulsion obtained has a mean particle size of greater than 10 micrometers, with droplets of approximately 1 mm.

EXAMPLE 23

The operation described in Example 16 is repeated from
on the one hand,
- 3 g of sodium dodecyl sulphate with an HLB value greater than 20
- 4 g of water and, on the other hand, 93 g of α,ω-bis(trimethyl) polydimethylsiloxane oil having a viscosity of 30 Pa·s (47 V 30000 oil).

The emulsion obtained has a mean particle size of 2.04 micrometers.

EXAMPLE 24

The operation described in Example 16 is repeated from
on the one hand,
- 3 g of sodium dodecyl sulphate
- 3 g of water and, on the other hand, 94 g of α,ω-bis(trimethyl) polydimethylsiloxane oil having a viscosity of 30 Pa·s (47 V 30000 oil).

The emulsion obtained has a mean particle size of 1.67 micrometers.

EXAMPLE 25

The operation described in Example 16 is repeated from
on the one hand,
- 3 g of tetradecyltrimethylammonium bromide with an HLB value>than 20
- 4 g of water and, on the other hand, 93 g of α,ω-bis(trimethyl) polydimethylsiloxane oil having a viscosity of 30 Pa·s (47 V 30000 oil).

The emulsion obtained has a mean particle size of 2.13 micrometers.

EXAMPLE 26

The operation described in Example 16 is repeated from
on the one hand, 7 g of an aqueous phase, the viscosity of which, at a shear gradient of $1\ s^{-1}$, is 100 Pa·s, which aqueous phase contains
- 2 parts by weight of sodium dodecyl sulphate
- 5 parts by weight of water
- 2% by weight of Natrosol 250 HR® (hydroxyethyl cellulose marketed by Hercules)

and, on the other hand, 93 g of 47 V 30000 oil.

After stirring for 45 minutes, the emulsion obtained has a mean particle size of 2.84 micrometers.

EXAMPLE 27

The operation described in Example 16 is repeated from
on the one hand, 7 g of an aqueous phase containing
- 2 parts by weight of sodium dodecyl sulphate
- 5 parts by weight of water
- an amount of Natrosol 250 HR® (hydroxyethyl cellulose, known hereinafter as HEC) such that the viscosity of the aqueous phase is at least equal to that of silicone oil;

and, on the other hand, 93 g of α,ω-bis(trimethyl) polydimethylsiloxane oil having a viscosity of 5 Pa·s (47 V 5000 oil).

The mean particle size of the emulsion obtained after stirring for 45 minutes is given in Table 5.

TABLE 5

| % of HEC in the aqueous phase | 0 | 1.14 | 2.00 |
|---|---|---|---|
| viscosity of the aqueous phase at $1\ s^{-1}$ (in Pa.s) | 0.009 | 11 | 90 |
| mean particle size (in micrometers) | 3 | 1.4 | 1.2 |
| particle size distribution width (in micrometers) | 4.7 | 1.7 | 1.5 |

The emulsion formed without addition of HEC in the aqueous phase is crude because the viscosity of this continuous phase is much less than that of the emulsified silicone oil.

EXAMPLE 28

The following are introduced into a 10 liter Neulinger® turbine planetary mixer (marketed by Neulinger):

- 2,500 g of 48 V 175000 oil
- 250 g of Cemulsol NP 9.

The medium is stirred for 6 minutes using the planetary system at 60 revolutions/minute and using the turbine at 500 revolutions/minute.

82 g of water are introduced with stirring over approximately 5 min, which corresponds to a water/water+surface-active agent ratio by weight of 0.25, and then the kneading operation is resumed as above for 100 min.

The development in the mean particle size of the emulsion as a function of the kneading time is given in Table 6.

The final emulsion is then diluted with 1467 g of water so as to adjust its solids content to 62.7%.

TABLE 6

| duration of kneading after introduction of the water (in minutes) | temperature (° C.) | mean particle size (in nanometers) |
|---|---|---|
| 10 | 27 | 792 |
| 17 | — | 647 |
| 40 | 43 | 511 |
| 100 | 35 | 438 |

EXAMPLE 29

The following are introduced into a 250 cm$^3$ reactor equipped with a scraping paddle stirrer system:

6.3 g of Cemulsol NP 10®

7.7 g of water

The mixture is stirred at 150 revolutions/min for 5 minutes.

A thick paste is formed to which are added, using a push pump situated at the bottom of the reactor, 86 g of Gomme 761® (polydiphenyldimethylsiloxane gum marketed by Rhône-Poulenc), over approximately 20 minutes, with stirring at approximately 350 revolutions/min. At the end of the introduction of the oil, the mixture is introduced into the trough of a Brabender® farinograph (marketed by Brabender) equipped with two scraping kneading helices and kneaded for 30 min. An emulsion having [lacuna] and a particle size of 2.4 μm is obtained.

This emulsion is then diluted with water until a solids content of 50% is obtained.

EXAMPLE 30

1.42 parts by weight of the viscous silicone oil emulsion of Example 3 are introduced into a shampoo conditioner formulation of the following composition:

36.0 parts by weight of sodium laureth sulphate*

2.0 parts by weight of lauramide DEA*

2.0 parts by weight of glycol distearate*

1.50 parts by weight of PEG 6000 distearate*

0.35 part by weight of Rhodicare D® xanthan gum* marketed by Rhône-Poulenc 0.65 part by weight of Jaguar HP 60® hydroxypropyl guar gum* marketed by Rhône-Poulenc 0.5 part by weight of preserving agent 0.25 part by weight of fragrance 0.25 part by weight of Alkamuls® polysorbate 20* marketed by Rhône-Poulenc an amount of distilled water which makes it possible to obtain 100 parts by weight of final composition (viscous oil emulsion+shampoo formulation).

[* C.T.F.A. (Cosmetic, Toiletry and Fragrance Association) name used in the cosmetics and body hygiene profession]

It is observed that the introduction of the viscous silicone oil emulsion facilitates combing and styling of dry or wet hair, increases the sheen of dry hair and improves the drying of wet hair.

EXAMPLE 31

1.16 parts by weight of the silicone oil emulsion of Example 18 are introduced into a mild shampoo conditioner formulation of the following composition:

36.0 parts by weight of sodium laureth sulphate*

4.0 parts by weight of Miranol C2M CONC NP® disodium cocoamphodiacetate* marketed by Rhône-Poulenc 2.0 parts of lauramide DEA*

2.0 parts by weight of glycol distearate*

0.50 part by weight of PEG 6000 distearate*

0.35 part by weight of Rhodicare D® xanthan gum* marketed by Rhône-Poulenc 0.65 part by weight of Jaguar HP60® hydroxypropyl guar gum* marketed by Rhône-Poulenc 0.5 part by weight of preserving agent 0.25 part by weight of fragrance 0.25 part by weight of Alkamuls® polysorbate 20* marketed by Rhône-Poulenc an amount of distilled water which makes it possible to obtain 100 parts by weight of the final composition (viscous oil emulsion+shampoo formulation).

It is observed that the introduction of a viscous silicone oil emulsion facilitates combing and styling of dry or wet hair and improves drying of wet hair.

EXAMPLE 32

2.0 parts by weight of the silicone gum emulsion of Example 29 are introduced into an anti-sun cream formulation of the following composition:

10.0 parts by weight of Marcol 52® mineral oil marketed by Exxon 5.0 parts by weight of jojoba oil*

10.0 parts by weight of isopropyl palmitate 5.0 parts by weight of 1,2-propanediol 3 parts by weight of U-V Rodialux A® screening agent marketed by Rhône-Poulenc 3 parts by weight of U-V Rodialux S® screening agent marketed by Rhône-Poulenc 0.5 part by weight of preserving agent 15.0 parts by weight of Tefose 63® emulsifying base marketed by Gattefosse 0.25 part by weight of fragrance 0.25 part by weight of Alkamuls® polysorbate 20* marketed by Rhône-Poulenc an amount of distilled water which makes it possible to obtain 100 parts by weight of the final composition (gum emulsion+cream formulation).

It is observed that the introduction of silicone gum emulsion increases the persistence of the U-V screening agents on the skin; the screening activity of this cream is maintained even after a prolonged bathe.

EXAMPLE 33

1.16 parts by weight of the silicone oil emulsion of Example 18 are introduced into a shaving foam formulation of the following composition:

4.8 parts by weight of stearic acid 1.2 parts by weight of coconut fatty acid 2.65 parts of triethanolamine 3.0 parts by weight of propylene glycol 4.5 parts by weight of glycerol 0.25 part by weight of fragrance 0.25 part by weight of Alkamuls® polysorbate 20* marketed by Rhône-Poulenc 10.0 parts by weight of propellant (3.2 bar)

an amount of distilled water which makes it possible to obtain 100 parts by weight of a final composition (viscous oil emulsion+shaving foam formulation)

It is observed that the introduction of the viscous silicone oil emulsion makes it easier for the razor to glide over the skin, decreases the irritation due to the razor and gives the skin a very soft feel after shaving.

EXAMPLE 34

1.42 parts by weight of the silicone oil emulsion of Example 3 are introduced into a styling mousse formulation of the following composition:

- 1.5 parts by weight of Mirataine CB® cocamidopropyl betaine* marketed by Rhône-Poulenc
- 1.5 parts by weight of Mirataine BET-O-30® oleamidopropyl betaine* marketed by Rhône-Poulenc
- 4.0 parts by weight of Polycare 133® polymethacrylamidopropyltrimonium chloride* marketed by Rhône-Poulenc
- 1.0 part of Silbione 70646® silicone oil (dimethicone copolyol) marketed by Rhône-Poulenc
- 0.5 part of preserving agent
- 0.25 part by weight of fragrance
- 0.25 part by weight of Alkamuls® polysorbate 20* marketed by Rhône-Poulenc
- 10.0 parts by weight of propellant (3.2 bar)
- an amount of distilled water which makes it possible to obtain 100 parts by weight of a final composition (viscous oil emulsion+styling mousse formulation).

It is observed that the introduction of viscous silicone oil emulsion makes it possible to improve the combing, styling and sheen of hair.

EXAMPLE 35

The mixture defined by the following composition is considered:

| | |
|---|---|
| 48 V 70000 silicone oil | 100 parts (a) |
| cemulsol NP 9 | 10 parts (b) |
| water | 6.7 parts (c) |

The mixing tool employed is a corotating twin screw marketed by the Company Liestritz. The longitudinal screw axes are parallel and rotate in the same direction. The screws comprise two threads and are self-cleaning. The screws have a diameter of 34 mm and the L/D ratio is 45 (L represents the length of each screw and D the diameter). L and D are expressed in the same unit. The rate of rotation can vary from 0 to 380 revolutions/min and the tangential speed of the screw of the extruder can reach 1.2 mis. The extruder is equipped at its end with a die with a diameter of 9 mm.

In this example, the extruder is cooled by forced circulation of cold water at a temperature of between 20° C. and 25° C. The rate is set at 350 revolutions/min. The total flow rate of the constituents is 11 kg/h. The ingredients are continuously and simultaneously introduced into the extruder according to the ratios defined in the composition.

The oil (a) and the cemulsol (b) are injected separately but at the same point into the extruder at an upstream position. The water is introduced downstream with respect to the point of incorporation of the oil and the cemulsol. The oil and the cemulsol are injected into the most upstream region onto screws comprising conveying components followed by a region of kneading components. The water is incorporated on a region of conveyor components completed by a kneading region. The screw then comprises an alternation of conveyor regions and kneading regions.

The mean particle size of the emulsion is measured using a Coulter N4S particle sizer. Its value is 0.38 μm.

EXAMPLE 36

A composition mixture identical to Example 35 is considered. The twin-screw extruder is identical to that described in Example 35 but with an L/D ratio of 15. The total flow rate is 11 kg/h and the rate set at 350 revolutions/min. The mean particle size of the aqueous emulsion is 0.4 μm.

EXAMPLE 37

The mixture with the following composition is considered:

| | |
|---|---|
| 48 V 70000 oil | 100 p |
| cemulsol | 2.5 p |
| water | 6.7 p. |

The extruder is analogous to that described in Example 36. The mean particle size is 2.71 μm.

We claim:

1. A cosmetic composition comprising an aqueous emulsion of organopolysiloxane s selected from the group consisting of silicone oils, gums, resins and mixtures thereof, said aqueous emulsion of organopolysiloxanes being prepared by a process consisting essentially of the step of kneading a mixture of (i) 100 parts by weight of a silicone phase having a dynamic viscosity at 25° C. at least equal to 3 Pa·s or having a consistency expressed in tenths of a millimeter per minute, as measured by a penetrometer at 25° C., of less than 2,000, said silicone phase comprising at least one polyorganosiloxane oil, gum, resin or mixture thereof; (ii) 2 to 20 parts by weight of water; and (iii) either 3 to 20 parts by weight of one or more surface-active agents or a combination of 0.5 to 10 parts by weight of at least one surface-active agent and $2.5 \times 10^{-4}$ to 20 parts by weight of at least one water-soluble thickening polymer having a mass greater than 10,000 g/mol, wherein said one or more surface-active agents have an HLB value of at least 10 and the relative amounts of components (ii) and (iii) are such that the viscosity or the consistency of said mixture of components (ii) and (iii) is greater than about one-tenth of the viscosity or consistency of said silicone phase (i); wherein said entire kneading step is carried out for a period of time in a mixer equipped with one or more stirrers in which the moving part of said one or more stirrers does not rotate at more than 500 revolutions/min with a tangential speed at the end of the moving part not exceeding 2.5 m/s so as to produce an oil-in-water emulsion having a particle size of 0.1 to 5 micrometers, and with the proviso that when a mixture of surface-active agents comprising at least one non-ionic surface-active agent is employed, said kneading is carried out in a single step.

* * * * *